United States Patent
Bihari

(10) Patent No.: US 6,384,044 B1
(45) Date of Patent: May 7, 2002

(54) METHOD OF TREATING CANCER OF THE PROSTATE

(76) Inventor: Bernard Bihari, 29 W. 15th St., New York, NY (US) 10011

(*) Notice: Subject to any disclaimer, the term of this patent is extended or adjusted under 35 U.S.C. 154(b) by 0 days.

(21) Appl. No.: 09/715,101

(22) Filed: Nov. 20, 2000

Related U.S. Application Data

(60) Provisional application No. 60/167,677, filed on Nov. 29, 1999.

(51) Int. Cl.⁷ .............................................. A61K 31/44
(52) U.S. Cl. ..................................... 514/282
(58) Field of Search ..................... 514/2, 282

(56) References Cited

U.S. PATENT DOCUMENTS 6,136,780 A * 10/2000 Zagon et al. ................... 514/2

OTHER PUBLICATIONS

Balzano et al, Clin. Endocrinol., vol. 27 #4, pp. 491–9 (abstract) Oct. 1987.*
Moon, Biochem. Biophys. Res. Commun., vol. 153, #2, pp. 722–7 (abstract), Jun. 1988.*
Kampa et al, Eur. J. Pharmacol., vol. 335, #2–3, pp. 255–65 (abstract) Sep. 1997.*
Matuo et al, Adv. Exp. Med. Biol., vol. 324, pp. 107–14, (abstract), 1992.*
Koo et al, Anticancer Res., vol. 16, #4A, pp. 1893–8, (abstract) Jun. 1996.*

* cited by examiner

*Primary Examiner*—James H. Reamer
(74) *Attorney, Agent, or Firm*—William J. Daniel

(57) ABSTRACT

Cancer of the prostate in human male patients even at an advanced state with metastasis to other organs, is treated by the administration, preferably at bedtime, to the patient by a pharmacologically effective mode of an essentially pure opiate receptor antagonist, typified by Naltrexone and Naloxone, exerting substantially higher blocking action for Mu opiate receptor sites than against Delta opiate receptor sites at a low dose concentration which produces therapeutic results corresponding to those obtained by the administration of Naltrexone at a low dosage level in the range of 1.0 mg. to 10 mg. per day and at which Delta receptor blocking activity is at most small and Mu receptor blocking activity is substantial. Naltrexone is suitable for oral administration and is preferred.

17 Claims, No Drawings

METHOD OF TREATING CANCER OF THE PROSTATE

CROSS-REFERENCE TO PROVISIONAL APPLICATION

This application is a complete application of my provisional application Ser. No. 60/167,677, filed Nov. 29, 1999.

This invention relates to the treatment of cancer and is concerned more especially with treatment of cancer of the prostate gland in human males by administration of an essentially pure opiate receptor antagonist such as Naltrexone and Naloxone at a low level dosage.

SUMMARY OF RELATED DISCLOSURES USING ESSENTIALLY PURE OPIATE ANTAGONISTS

The use of an essentially pure opiate receptor antagonist in the treatment of several diseases has already been disclosed in patents in which I am named as an inventor. In U.S. Pat. No. 4,888,346, issued Dec. 19, 1989, the treatment was for the acquired immune deficiency syndrome (or AIDS) in any of its known states, including AIDS-related complex. In U.S. Pat. No. 5,013,739, issued May 7, 1991, the disease treated was chronic fatigue syndrome while in U.S. Pat. No. 5,346,900, issued Oct. 18, 1994, the disease was chronic herpes virus infections. In the latter patent, examples of treatment of multiple sclerosis and chronic inflammation of the connective tissue, such as arthritis and lupus, was also disclosed.

For the treatment of all these diseases, the amount of the essentially pure opiate receptor antagonist to be administered was required to be at a quite low level corresponding in results achieved thereby to those obtained by the administration of Naltrexone at a dosage level of from 1.0 mg. to 10 mg per day., preferably at a dosage level of 1.0 mg. to about 5 mg., and most preferably at about 3.0 mg per day. At dosage levels above about 10 mg per day, not only were the desired therapeutic results not obtained but the effect of the treatment appeared to be negative in exacerbating the disease.

In provisional application Ser. No. 60/108,838, filed Nov. 17, 1998, I disclosed that administration at a low dosage level of an essentially pure opiate receptor antagonist gives desirable therapeutic results in the treatment of a group of closely related malignancies known as lymphoproliferative syndrome, which includes malignant lymphoma, chronic lymphocytic leukemia, Hodgkin's disease (or Hodgkin's lymphoma), and non-Hodgkin's lymphoma. As the generic name suggests, these diseases are characterized by the multiplication or proliferation of tissue of the lymphatic system, especially lymphocytes (cells) produced in the lymph nodes. Lymphocytes are important components of the human immune response system and upon exposure to a foreign antigen in the human body naturally proliferate or multiply to combat the antigen. In this group of malignancies, the proliferation goes out of control, resulting in an abnormal level of lymphocytes in the blood stream, enlargement of the lymph nodes due to accumulation of the lymphocytes there, and other symptomatic characteristics. Administration of an essentially pure opiate receptor antagonist such as Naltrexone and Naloxone at a low level dosage appears by means of some up until now inexplicable mechanism to be useful in the treatment of this group of malignancies.

Finally, in provisional application Ser. No. 60/139,482, filed Jun. 17, 1999, I disclosed that administration at a low dosage level of an essentially pure opiate receptor antagonist gives desirable therapeutic results in the treatment of various cancers of the gastrointestinal tract including cancers of the esophagus, stomach, large and small intestines, rectum, pancreas and liver.

In addition to my prior disclosures identified above, the action of opiate receptor antagonists. exemplified by Naltrexone and Naloxone, when administered to a variety of living organisms, including tissue and cells, has been studied by Zagon et al in U.S. Pat. No. 4,689,332, among other patents and published papers. According to these studies, these antagonists can exert either a growth accelerating or a growth inhibiting effect dependent upon the length of time the opiate receptor sites of the organism are "completely and continuously" blocked or occupied by the antagonist. Specifically, a growth accelerating or promoting action occurs with blockage for a period of at least 12 hours per day, as can be achieved with a dosage of at least about 10 mg. and preferably about 20 mg. per day, whereas a growth inhibiting action occurs with blockage for only a period of about 2 to 12 hours per day, as can be achieved with a dosage of less than 10 mg. down to about 0.1 mg. per day.

The growth accelerating embodiment is said to be effective "to proliferation, migration, and differentiation of certain specific cells or tissue, including organ tissues, neural tissue, bone marrow, red blood cells, lymphocytes, liver cells, etc." (See patent, col. 9, lines 15–25.) This disclosure, however, is silent as to whether these any of these same "cells or tissues" can be subject to the growth inhibiting embodiment, the focus of the inhibiting embodiment disclosure paralleling the above excerpt being on weight loss of the organism as a whole. (See col. 9, lines 32–45 and col. 10, lines 45–59.)

In addition, the growth inhibiting aspect is described as "related to the prevention, treatment and control of cancer" (see col. 10, line 60—col. 11, line 47), the essential disclosure in this connection being as follows: "The action of the compounds of the invention can be employed to terminate the rapid growth patterns of cancer and related abnormalities. It should be understood, that a regime of the present compounds cannot dissipate or reduce a tumor mass or other metastasized growth. These compounds can only terminate the growth of the abnormal cells and inhibit the continued growth thereof. However, by preventing tumor growth to continue [sic], i.e. reducing the tumor burden, the body's own defense mechanism, i.e. the immune system, has the opportunity to rid the body of the cancerous growth whether benign or malignant. This aspect of the invention is particularly significant in light of early diagnostic techniques which do reduce tumor size, or with procedures for tumor excision. Moreover, naloxone, naltrexone, or the other related compounds can be administered as a prophylaxis to human or animal subjects who may be exposed to potentially carcinogenic agents."

The only cancer specifically identified in the patent for treatment by the Zagon etal concept is neuroblastoma in mice, which is illustrated by specific examples 2, 3, and 5, the only examples concerned with cancer. Neuroblastoma is a rather rare and special type of cancer, occurring in the sympathetic autonomous nervous system, i.e. mainly the nerves of the spinal column, and is essentially limited in occurrence to young children up to about 10 years of age. Evidence has been reported that neuroblastoma is peculiarly susceptible to natural immunobiological resistance. According to "IMMUNOBIOLOGY FOR THE CLINICIAN" by Barber, Copyright 1977, John Wiley & Sons, the lymphocytes of disease-free mothers of young neuroblastoma patients are able to kill neuroblastoma cells extracted from their diseased children but had no effect on normal tissue cells or tumor cells of other than neuroblastoma and lymphocytes of siblings of such patients also were able to kill neuroblastoma cells of the patients. (Cf p. 69). The same text states (at p. 102) that incidence of neuroblastoma nodules found by autopsy is "40–50 times greater" than the overall incidence of clinically diagnosed neuroblastoma. This obviously suggests that a competent immune system exerts a strong controlling action on neuroblastoma which is found in few if any other kinds of cancers.

While there is a tendency among the general public (and even the often equally uninformed media) to generalize among all "cancers", (a conception which unfortunately appears to be shared by Zagon et al) "cancer" is, in fact, a collection of many distinct malignancies, each with its unique characteristics, behavior, and treatment response (which is one reason for the tortuously slow progress in the treatment of "cancer"), and this individualistic nature is especially applicable in the case of neuroblastoma. One cannot, therefore, reasonably extrapolate from the response of neuroblastoma to a given prophylaxis to a supposition that an entirely different type of "cancer" will exhibit the same response and this conclusion is certainly valid in the case of malignancies of the prostate, which as discussed in the following exhibits characteristics shared by few if any other malignancies.

GENETAL OCCURRENCE OF AND RECOGNIZED THERAPIES FOR PROSTATE CANCER

According to "THE MERCK MANUAL OF MEDICAL INFORMATION—HOME EDITION", Copyright, 1997, Merck & Co., Inc., Whitehouse Station, N.J., pp. 1060, 1061, cancer of the prostate is almost incredibly common in males, especially older males. In fact, the incidence in men over 70 years of age is said to be 50% and in those over age 90 is virtually 100%. Not with standing this remarkable prevalence, the direct cause or causes of prostate cancer has not yet been identified and remains unknown, although there appears to be an association with testosterone production. By virtue of its location, prostate cancer is one of the so-called "hidden cancers", being rarely detected until it has reached an advanced stage. Except for a small proportion of an aggressive type, prostate cancer is characterized by an extreme slow-growth pattern which differentiates it from the vast majority of other kinds of cancer (and might even be reason for questioning if it satisfies the typical text-book definition of cancer as a rapidly proliferating growth). Thus, quite to the contrary of what would be expected from its virtual inevitability (assuming one survives other causes of mortality), the death rate from prostate cancer is considered to be relatively low at less than 3% although it is rated the second most common cause of cancer death among American men.

The presence of prostate cancer can sometimes be suspected from urinary difficulties, such as reduced flow or increased frequency of the need to urinate, but benign conditions can exhibit the same symptoms. A prostate specific antigen (PSA) has been identified and the level of this antigen is of some value in diagnosing the disease as it is usually high where the tumor is present. However, its correlation with the actual presence of the tumor is poor at best, giving a false-negative in about one out of three cases where cancer exists and a false-positive in about two out of three cases where there is no tumor. Elevated PSA levels alone, hence, are rarely a basis for initiating treatment but serve mainly as a signal for further evaluation. Microscopic examination and/or biochemical testing of tissue samples removed by biopsy is the most reliable evidence where digital manipulation or ultrasonic scanning reveals the existence of one or hard nodules or some other localized abnormality in the prostate gland. If the tumor has spread to other regions such as adjacent bone parts or organs, bone scans or X-rays can be useful in detecting metastasized tumors.

Treatment modality depends mainly on the extent of spread of the tumor, its type in terms of aggressiveness and the age of the patient. Where the cancer is localized and of the more common slow-growing variety, removal of the entire gland by surgery or radiation therapy can achieve an apparent cure. Both approaches, however, can be subject to important side effects including incontinence or impotence. A modified and less radical surgical procedure has been developed which can reduce either of these side effects but at the risk of a less successful outcome especially if the tumor tends to be of a more aggressive variety. Dependence of the cancer on normal testosterone production allows alternative treatments utilizing testosterone-inhibiting medications. However, these tend to be accompanied by certain feminizing consequences that may be repugnant to the male psyche and their beneficial results in a significant proportion of cases are of limited duration. In a similar vein is surgical removal of one or both testes which is more permanent but has psychological implications unacceptable to some men.

If the patient is of reasonably advanced age of 70 or older, where average life expectancy is curtailed by the likelihood of death from other causes, the balance between beneficial action on the tumor vs. undesirable restrictions on his life-style with any of these therapies is sufficiently negative that a do-nothing approach may be the best choice in many cases. If the cancer is already at an advanced stage when first detected, focus is on alleviating symptoms by one or more of the above options.

An approach totally different from the standard therapies for to prostate cancer is currently being explored in a very new study aimed at developing a vaccine for reducing the risk of reoccurrence of a previously treated prostate cancer before it has reached the stage deemed appropriate for such conventional therapies as surgical removal, radiation or hormonal administration has just been reported on page 5 of the "Medical Section" of the Washington Post dated Oct. 29, 1999. This report is based on a paper appearing in the October, 1999, issue of the journal Cancer Research, In this study, in order to create a vaccine, cancer cells are recovered from the tumor after surgical removal of the prostate and are subjected to biological alteration by the introduction therein of a gene identified as "GM-CFS" known to have an activating action on the human immune system increasing its ability of recognize "foreign" cancer cells. The tumorific capability of the gene-altered cancer cells is attenuated by radiation and the thus bio- and radio-modified cells are injected in the thigh of the same patient from whom they were removed. Four weeks later, the respective immune systems of the patients were evaluated and showed a distinct boost. Specifically, the B-cells "began producing antibodies against the prostate cancer cells" while the T-cells "began attacking the prostate tumor cells."

The concept of injecting into the patient a pathogenic antigen attenuated by radiation or otherwise in the hope of evoking an enhanced immune reaction against subsequent natural exposure to the pathogen has been known for many years. A vaccine against tuberculosis based on this concept utilizing the Bacilli Calmette Guerin (BCG) strain of Mycobacteria Bovis species of tuberculosis bacteria has been available for over 75 years (see Introduction of "Use of BCG in the Treatment of Human Neoplasms", by Nathanson, "Seminars in Oncology", Vol. 1, No. 4, (December), 1974, pp. 337–350), and has been inoculated into millions of individuals. However, according to THE MERCK MANUAL OF MEDICAL INFORMATION—HOME EDITION", supra, p. 1222, it is not widely used in the United States because it is not 100% effective and by permanently creating tuberculosis antibodies in the patient's system makes it impossible to carry out subsequent testing of the individual for tuberculosis.

More to the point here, as the body of the Nathanson survey summarizes from its 136 referenced articles collected through 1974, the possibility of using BCG in some form, usually attenuated, as a non-specific immunmo-prophylactic against a wide variety of human cancers has been extensively examined in numerous animal studies. There is no doubt that BCG on injection is capable of provoking a non-specific (as well as specific) immuno-potentiating effect on the human immune system but the practical application of that effect against cancer remains highly problematic, despite years of experimentation. As summarized by Nathanson and similar reviews, the therapeutic results described for these studies are mixed at best and are often difficult to judge due to lack of controls for comparison or somewhat contradictory results in subsequent studies. Furthermore, the subjects frequently experienced complications of varied seriousness including symptoms of tuberculosis, localized ulcerations, hypersensitivity reactions and so on. dependent somewhat on the mode or administration. The author concludes that utilization of the BCG treatment is "clearly hazardous" for those having a depressed immune system, a previous exposure to BCG or rapidly progressive disease.

In the light of this evidence relating to the use of BCG as a counteractant to cancers, it is plainly evident that the above current report of tests of the gene-altered cancer cell vaccine must be viewed with considerable caution. Immune system response after a period of only four weeks and for so small a group does not allow for possible long-term consequences and/or large group variations.

In any event, the vaccine in question involves a technically complex (and presumably expensive) procedure that must be individualized to each patient which certainly limits its general application.

DESCRIPTION OF THE INVENTION

I have now discovered that cancer of the prostate gland even when in an advanced stage can respond to an entirely different therapeutic approach involving the administration of an essentially pure opiate receptor antagonist at a dosage corresponding to the same low quantitative level that was found useful for the treatment of the disorders disclosed in my prior patents and applications identified above, In the patents, the diseases in question were of a totally different nature free of any malignant behavior and while my prior provisional applications were in some instances directed to treatment of certain malignancies, these malignancies have no apparent relation to prostate cancer.

The possibility of the administration of an essentially pure opiate receptors antagonist of the invention inducing an enhancement of the immune system of patients to which they are administered has been generally disclosed before by me but it could not have imagined that an enhancement by means of a simple medication could bring about remarkable remission of an existing prostate cancer. This is all the more true in view of the findings of Zagon etal, supra, which, in the first place, expressly disavow potential efficacy of such antagonists against established tumors masses especially when accompanied by metastasis and, in the second place, were tested against neuroblastoma cancer which has no discernable relation to prostate cancer. Furthermore, the totally different approach taken in the latest study reported above confirms how unlikely is any realization of this invention by those actually involved in finding a new treatment for prostate cancer.

Naltrexone and Naloxone are presently the only essentially pure opiate receptor antagonist drugs known to have received government approval for administration to humans, but in the event drugs exist or should be developed exhibiting the same preferential or selective affinity for Mu over Delta opiate receptor sites, they to should be effective for purposes of the present method and are within the scope of the invention. For more details of this selective or preferential action, reference may be had to U.S. Pat. No. 5,013,739, the relevant portions of which, in particular col. 5, line 17—col. 6, line 25, are incorporated by reference.

Likewise, while the dosage levels are been specified here, more complete information as to dosage level which is applicable to the present invention, is given in the same -739 U.S. patent, especially col. 6, line 59—col. 7, line 17, which is incorporated by reference.

As delineated in the above passages of my -739 patent, it is important that the dosage level be controlled to a relatively low level which is generally in the range of about 1 mg to about 10 mg. per day for humans for Naltrexone and a corresponding range in terms of therapeutic effectiveness when other essentially pure antagonists are substituted. A preferred dosage is correlated to the action of the antagonist on certain specific groups of opiate receptors, taking advantage of a selectively higher blocking action of the antagonist against Mu opiate receptors than against Delta receptors, by utilizing an amount which does not override this selective blocking action but is effective to exert a substantially higher opiate blocking action against Mu receptors than against Delta receptors.

Most preferred is the selection of an amount of the essentially pure opiate antagonist that is at a level within the above range at which the antagonist exerts an opiate blocking action substantially exclusively for Mu opiate receptors over Delta opiate receptors. That is, the amount is such that the antagonist does exert a substantial blocking action for Mu opiate receptors but does not exert such an action against Delta opiate receptors.

Given that as Naltrexone is available in a form suitable for oral administration and is recognized to be effective when so administered, it is preferred that Naltrexone be utilized as the opiate antagonist and be administered orally. But where alternative administration routes are effective, they, in principle, are not precluded and can be employed. Naloxone, on the other hand, has not generally proven to be effective when administered orally; it is available in a form suitable for injection and is better administered by injection, It is also preferred that administration take place in the evening hours, and particularly at bedtime, since the action of the antagonist appears to develop more strongly when the patient is sleeping and at rest.

As demonstrated by the following examples, a particularly surprising, even remarkable, feature of the administration of the essentially pure opiate antagonist of the invention is the beneficial results achieved thereby when the prostate cancer is in an advanced stage at which other therapies have lost their effectiveness or would serve only a palliative purpose to reduce pain or otherwise make the patient more comfortable until the inevitable occurs. In the past, once the prostate cancer has metastasized to other regions of the body or exhibited strongly positive symptoms of re-occurrence following a substantial period of remission, very little if any hope existed of accomplishing any persistent or long-lasting reduction in the extent of the cancer.

In distinct contrast, the treatment of this invention has proved effectual in achieving after the tumor has metastasized or after a considerable period of remission brought about with conventional therapies (as established by absence of apparent symptoms) but has then re-occurred, at least substantial, if not full, elimination of the cancer, at least to the extent it can be detected by means of the usual symptoms, for long periods of time.

This is not to say that the treatment of the invention could not be combined with other treatment modalities, including testosterone-blocking hormonal therapies or radiation. In the face of a strongly negative prognosis, a patient would understandably be motivated to press for relief by any and all possibilities. Similarly, the present treatment could be undertaken immediately after conventional surgery or course of radiation, to serve an adjuvant role.

Certain of the examples also demonstrate that favorable results can be achieved when the treatment of this invention is carried out before any conventional mode of treatment has been adopted. Of course, conventional radiation or administration of an anti-hormone medication can be added at any time with a reasonable expectation of increasing the attrition of the tumor.

EXAMPLES

Example 1

A 63 year-old man consulted his physician is December 1993, complaining of mild obstruction of urine flow. A prostate specific antigen test was carried out with a result of 15 and a sonogram revealed enlargement of three lymph nodes. Treatment was initiated with flutamide plus leuprolide according to the usual protocol and follow-up readings of PSA showed a drop to zero. Periodic measurement of PSA were made and after four years, a substantial increase was observed over a six month period. A bone scan was conducted and showed the presence of tumor in the lower vertebrae and several ribs. It was concluded that the tumor had become resistant to drug therapy and treatment with flutamide plus leuprolide discontinued. Instead, a course of radiation of the involved ribs and lumbar-sacral vertebrae was carried out to reduce pain, following which the patient was referred for further treatment. He was started on naltrexone at a dosage of 3 mg/day q.h.s and after four months of the naltrexone treatment, his PSA level dropped to less than 1.0. Bone scans revealed the tumor to have disappeared and he was free of other symptoms. He has continued to the symptom-free in follow-ups over the subsequent 18 months with normal bone scans and very low PSA readings, suggesting that remission of the tumors has been achieved.

Example 2

A 71-year old man during a routine physical examination in 1992 showed a PSA level of 18.0. On digital rectal examination, a hard tumor mass was found in the prostate. Bone X-rays were normal and a sonogram showed no evidence of any tumor spread outside the prostate capsule. He was treated with flutamide plus leuprolide for eight weeks followed by implantation of a radioactive needle into the tumor mass. This resulted in disappearance of the tumor mass and reduction in PSA level to zero. The drug therapy was continued routinely but five years later in 1997, routine testing showed a sustained rise in PSA level. Bone scans revealed the presence of lesions in his lumbar vertebrae and pain was experienced there. At this point, drug therapy was terminated and local radiation was applied to the lumbar spine to reduce pain. Lumbar X-rays taken after radiation showed a modest decrease in the extent of metastatic tumor. Since the tumor was judged at this point to be resistant to conventional therapies, the patient was referred for special follow-up. He was started on low-dose naltrexone 3 mg. day q.h.s. Over the next five months, his PSA reading dropped to zero, X-rays of the spine became normal and all clinical signs of the tumor disappeared. The low-dose naltrexone treatment has continued and he has remained free of tumor.

Examples 3 and 4

Two acquaintances in their sixties had been routinely monitoring their PSA levels every six to twelve months because of their age. Then, about six years ago for one and eight years for the other, one test showed a marked rise in PSA levels above normal for each and on digital rectal examination, a hard tumor mass was found in each. Biopsies of the masses were performed by a urologist and proved positive for adenocarcinoma of the prostate. Both were started immediately on low-dose naltrexone 3 mg/day q.h.s while they considered the desirability of undergoing standard therapies for prostate cancer. This exploration took a period of three months for one and four months for the other with both eventually electing to undergo treatment with flutamide, a testosterone blocking agent. On consultation with the urologist to begin administration of flutamide, each was advised that their respective tumors had already undergone substantial shrinkage, by more than one-half. Both began the anti-testosterone therapy while maintaining the low-dose naltrexone treatment, and after three months, their PSA levels had dropped to zero and the tumor masses had shrunk until they were no longer palpable by rectal examination, Both have continued the combination of low-dose naltrexone and flutamide and up until now there have been no signs or symptoms in either of reoccurrence of the prostate cancer.

In the course of the preceding description, reference has been made to certain alternatives or variations in the practice of the invention and it would be understood that others are conceivable. It is intended that all such modifications are within the scope of the invention except as positively excluded from the ambit of the appended claims.

Having thus described my invention, that which is claimed is:

1. A method of treating cancer of the prostate in a human male patient, which comprises the step of administering by a pharmacologically effective mode to such patient a therapeutically effective dose of a therapeutic agent consisting essentially of an essentially pure opiate receptor antagonist, the amount of said dose being selected to produce therapeutic results substantially corresponding to those produced by Naltrexone when administered in the range of about 1 mg to about 10 mg per day.

2. The method of claim 1 wherein said opiate receptor A antagonist is Naltrexone or Naloxone.

3. The method of claim 1 wherein said opiate receptor antagonist is administered during the evening hours.

4. The method of claim 1 wherein said opiate receptor antagonist is Naltrexone and is administered in an amount within the range of 1 mg to 10 mg/day.

5. The method of claim 1 wherein the prostate cancer to be treated is in an advanced stage.

6. The method of claim 5 wherein said prostate cancer to be treated has metastasized to other regions of the patient's body than the prostate gland.

7. The method of claim 5 wherein said prostate cancer to be treated has re-occurred in the patient following a significant period of remission.

8. The method of claim 1 wherein said prostate cancer is treated by the administration of said antagonist prior to the utilization of any conventional therapy against prostate cancer.

9. A method of treating cancer of the prostate in a male human patient, which comprises the step of administering by a pharmacologically effective mode to such patient a therapeutic agent consisting essentially of an essentially pure opiate receptor antagonist having a selectively higher blocking action against Mu opiate receptors than against Delta receptors in an amount which is effective to exert a substantial opiate blocking action against Mu receptors but insufficient to exert such action against Delta receptors.

10. The method of claim 9, wherein said opiate receptor antagonist is either Naltrexone or Naloxone.

11. The method of claim 10 wherein said opiate receptor antagonist is Naltrexone.

12. The method of claim 11 wherein said opiate receptor antagonist is administered in an amount within the range of 1 mg to 10 mg/day.

13. The method of claim 9 wherein said opiate receptor antagonist is administered during the evening hours.

14. The method of claim 9 wherein the prostate cancer to be treated is in an advanced stage.

15. The method of claim 14 wherein said prostate cancer to be treated has metastasized to other regions of the patient's body than the prostate gland.

16. The method of claim 14 wherein said prostate cancer to be treated has re-occurred in the patient following a significant period of remission.

17. The method of claim 9 wherein said prostate cancer is treated by the administration of said antagonist prior to the utilization of any conventional therapy against prostate cancer.

* * * * *